(12) United States Patent
Zhang et al.

(10) Patent No.: US 9,618,484 B2
(45) Date of Patent: Apr. 11, 2017

(54) GENERAL SAMPLE INJECTOR, GAS CHROMATOGRAPH AND COMBINED SPECTROMETER

(71) Applicant: NUCTECH COMPANY LIMITED, Beijing (CN)

(72) Inventors: Qingjun Zhang, Beijing (CN); Yuanjing Li, Beijing (CN); Zhiqiang Chen, Beijing (CN); Qiufeng Ma, Beijing (CN); Ziran Zhao, Beijing (CN); Yinong Liu, Beijing (CN); Yaohong Liu, Beijing (CN); Junxiao Wang, Beijing (CN); Xiang Zou, Beijing (CN); Yanchun Wang, Beijing (CN); Jianping Chang, Beijing (CN); Linxia Tan, Beijing (CN)

(73) Assignee: Nuctech Company Limited, Beijing (CN)

( * ) Notice: Subject to any disclaimer, the term of this patent is extended or adjusted under 35 U.S.C. 154(b) by 159 days.

(21) Appl. No.: 14/577,603

(22) Filed: Dec. 19, 2014

(65) Prior Publication Data

US 2015/0185189 A1    Jul. 2, 2015

(30) Foreign Application Priority Data

Dec. 30, 2013  (CN) .......................... 2013 1 0746569

(51) Int. Cl.
*G01N 30/18*  (2006.01)
*G01N 30/12*  (2006.01)
(Continued)

(52) U.S. Cl.
CPC ........... *G01N 30/18* (2013.01); *G01N 27/622* (2013.01); *G01N 30/12* (2013.01);
(Continued)

(58) Field of Classification Search
CPC ........ G01N 30/12; G01N 30/18; G01N 30/20; G01N 30/30; G01N 30/7206; G01N 27/622; G01N 2030/025
See application file for complete search history.

(56) References Cited

U.S. PATENT DOCUMENTS

| | | | | | |
|---|---|---|---|---|---|
| 4,732,046 | A | * | 3/1988 | Lawrence | ............ G01N 1/4022 250/282 |
| 5,037,611 | A | * | 8/1991 | Ledford, Jr. | ........... G01N 30/16 250/288 |

(Continued)

FOREIGN PATENT DOCUMENTS

| CN | 1352390 A | 6/2002 |
|---|---|---|
| CN | 203216933 U | 9/2013 |

OTHER PUBLICATIONS

Machine translation of CN1352390 downloaded Jul. 20, 2016.*

*Primary Examiner* — Natalie Huls
(74) *Attorney, Agent, or Firm* — McDermott Will & Emery LLP

(57) ABSTRACT

The present invention discloses a general sample injector, comprising a sample injection port mechanism, a sample injector shell, a vaporizing chamber, a heater, a temperature control unit, a carrier gas channel, a septum purge channel, a flow splitting channel, a coolant channel, a multichannel flow control valve and a temperature control unit. The general sample injector, equivalent to a "programmed temperature vaporizer" injector combining splitting/no splitting with cold column head sample injection, gives full play to the advantages of various sample injection modes, overcomes a plurality of disadvantages, and has higher practicability and better flexibility.

18 Claims, 1 Drawing Sheet

(51) Int. Cl.
  *G01N 30/72*   (2006.01)
  *G01N 27/62*   (2006.01)
  *G01N 30/20*    (2006.01)
  *G01N 30/30*    (2006.01)
  *G01N 30/02*    (2006.01)

(52) U.S. Cl.
  CPC ......... *G01N 30/7206* (2013.01); *G01N 30/20* (2013.01); *G01N 30/30* (2013.01); *G01N 2030/025* (2013.01)

(56) References Cited

U.S. PATENT DOCUMENTS

| | | | | |
|---|---|---|---|---|
| 5,686,656 A * | 11/1997 | Amirav | ............... | G01N 30/12 73/23.41 |
| 5,778,681 A * | 7/1998 | Li | ............... | G01N 30/12 62/50.2 |
| 5,827,353 A * | 10/1998 | O'Neil | ............... | G01N 30/08 95/87 |
| 6,093,371 A * | 7/2000 | Wilson | ............... | G01N 30/12 422/502 |
| 6,245,298 B1 * | 6/2001 | Bremer | ............... | G01N 30/12 422/307 |
| 6,494,939 B1 * | 12/2002 | Tipler | ............... | G01N 30/10 96/105 |
| 6,907,796 B2 * | 6/2005 | Bremer | ............... | G01N 30/12 219/628 |
| 2007/0157709 A1 * | 7/2007 | Gamble | ............... | G01N 35/10 73/61.55 |
| 2014/0331744 A1 * | 11/2014 | Van Egmond | ............... | G01N 30/12 73/23.41 |

* cited by examiner

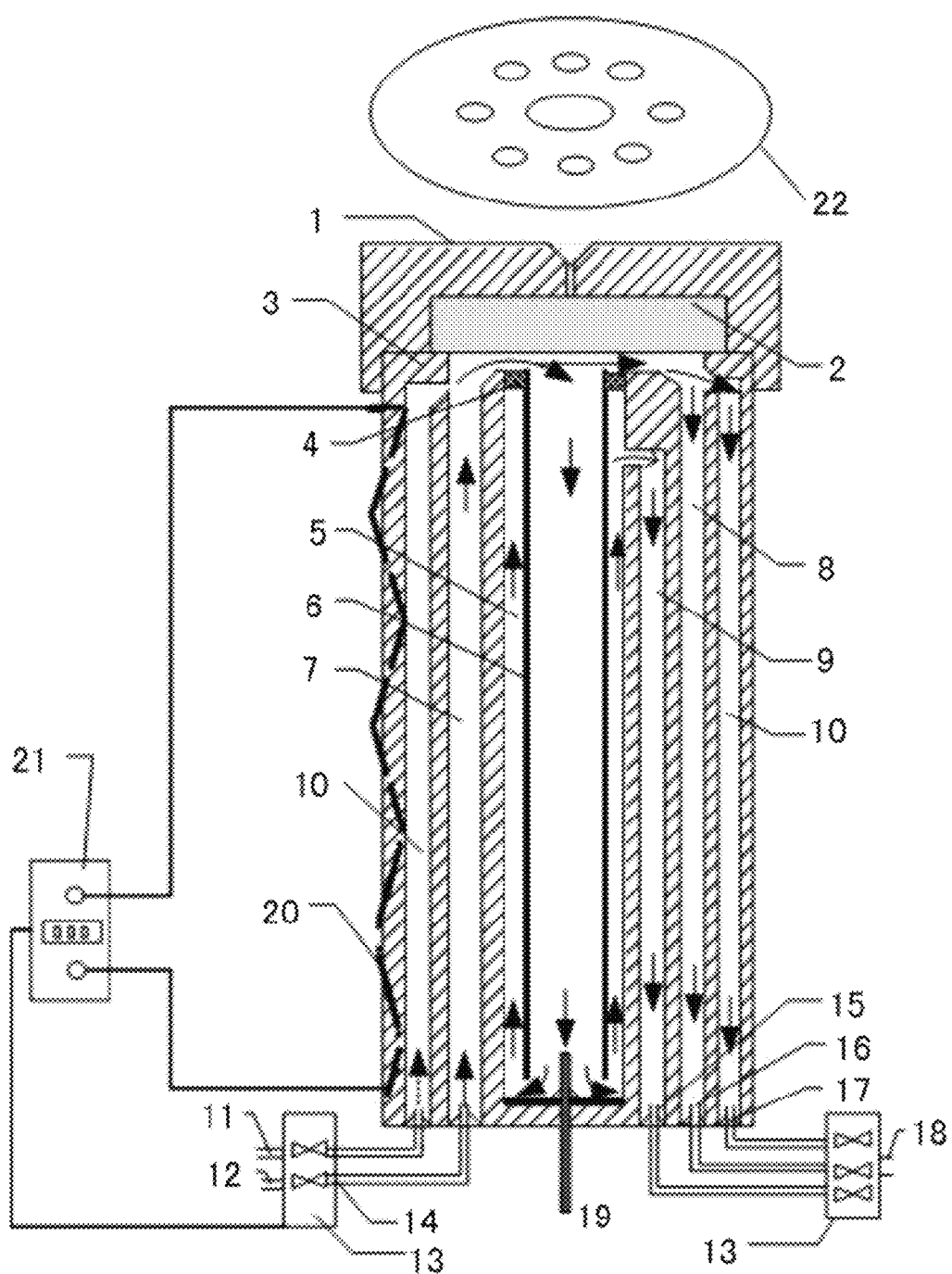

GENERAL SAMPLE INJECTOR, GAS CHROMATOGRAPH AND COMBINED SPECTROMETER

CROSS-REFERENCE TO RELATED APPLICATION

This application claims priority to and the benefit of Chinese Patent Application No. 201310746569.8 filed in the State Intellectual Property Office of the P.R.C (SIPO) on Dec. 30, 2013, the entire contents of which are incorporated herein by reference.

TECHNICAL FIELD

The present invention belongs to the field of analysis and detection, and relates to a sample injector for a gas chromatography or a gas chromatography-ion mobility spectrometer and particularly to a split/splitless programmed temperature sample injector for capillary columns.

BACKGROUND

During the analysis process of a sample by using Gas Chromatography (GC) or a GC combined to ion mobility spectrometer (IMS)/Mass Spectrometer (MS), the sample passes through a sample injector first. The sample injector is used for rapid vaporizing the liquid or solid sample of interest at a first place and then feeding the sample vapor to a GC column head quickly, accurately and quantitatively after mixing and diluting with the carrier gas. Since the first capillary column has been produced by Perkin Elmer, due to its advantages of high column efficiency and good separation performance, there has been already more than 90% of GC analysis realized by capillary columns nowadays ("Basic Gas Chromatography", Second Edition, by Harold M. McNair and James M. Miller. Copyright© 2009 John Wiley & Sons, Inc.). Due to the characteristic of small capacity of a capillary column itself, split/splitless sample injectors have become the most common sample injectors for GC, GC-IMS or GC-MS.

There have been mature split/splitless sample injectors at present. However, as different sample components have different actual split ratios, under a certain set separation ratio, the component entering a chromatographic column (capillary column) will be different from the original sample component so as to result in split discrimination (especially for samples having a wide boiling range), so that the accuracy of analysis is influenced to result in poor quantification and complexity.

There are mainly three aspects for the cause of the split discrimination:

First, non-uniform heating temperature distribution of a vaporizing chamber: in some cases, a difference between the temperature at the center of the vaporizing chamber and the temperature at two ends thereof is very large, so the sample is not vaporized uniformly or components having different boiling points are coagulated at positions below the point of vaporization point after being vaporized.

Second, the carrier gas is not preheated: the carrier gas will have a change in temperature gradient after entering the vaporizing chamber, so the vaporization rates of different components of the sample will be different; as the time the sample enters the chromatographic column from vaporizing in the vaporizing chamber is very short (in seconds), so that the split flow is far larger than the flow in the column, and thus the components not fully vaporized may split more samples than the components fully vaporized.

Third, different sample components have different diffusion rates in the carrier gas; however, the diffusion rate is in direct proportion to the temperature, so vaporizing the sample as quick as possible is an important measure for reducing split discrimination. Therefore, the temperature of the sample injector must be strictly controlled and is slightly higher than the temperature of the column oven; thus, the manufacturing cost of the sample injector is improved, and it is disadvantageous for the analysis of thermally instable substances.

Patent No. CN1352390A has disclosed a sample injector for solving the preheating problem of carrier gas. In the sample injector, a carrier gas preheating chamber is provided between a split flow exporting channel and a vaporizing chamber, a carrier gas inlet is communicated with the lower portion of the carrier gas preheating chamber, and the upper portion of the carrier gas preheating chamber is communicated with the vaporizing chamber. The carrier gas enters the carrier gas preheating chamber from the inlet and then moves upward after preheated, and then enters the vaporizing chamber from the top to contact a sample and vaporize the sample instantly. Although such a sample injector port solves the preheating problem of carrier gas and the problem of split discrimination, the volume of the vaporizing chamber is increased equivalently as the preheating chamber is communicated with the vaporizing chamber, that is, the pre-column dead volume is increased. Thus, the vaporized sample mixture gas will be diffused back to the preheating chamber, thereby increasing retention time (RT) and broadening peak.

To overcome the problems in the patent CN1352390A, Patent No. CN203216933U has disclosed a sample injector for non-volatile substances, including a shell and a diffusion tube disposed inside the shell. A carrier gas channel communicated with the diffusion tube is provided on an end cover of the shell. The carrier gas channel extends to the inside of the diffusion tube and has a certain distance away from the bottom of the diffusion tube. The advantage of this design is that, as the sample is placed on the bottom of the diffusion tube, the volatilization concentration on the surface is the highest during the volatilization of the sample; and the carrier gas channel extends above the surface of the sample, so the carrier gas may take away all the volatilized gas on the surface of the sample. In order to uniformly heat the upper and lower portions of the sample injector, electric bars extending from the bottom of the shell to the end cover are uniformly arranged around the shell of the sample injector, so that uniform heating of the upper and lower portions of the sample injector is realized. In the parent, the problem of non-uniform vaporizing of the sample is solved, but the sample injector has a splitless mode only. As the splitless sample injection mode has complicated operating conditions and high requirements for operation techniques, the splitless sample injection is far less common than the split sample injection in practice. Therefore, the splitless sample injection is taken into consideration only when the split sample injection cannot meet the analysis requirements (mainly requirements for sensitivity).

In addition, it is required to perform continuous sample injection when a detection task is heavy, and it is required to reset temperature of a sample injector in the case of an obvious difference between boiling ranges of samples at two adjacent times. Although there are various split/splitless sample injectors of different types, yet there are few general sample injectors capable of cooling fast. Therefore, in order to realize fast testing, it is necessary to add a fast cooling design and a temperature control design to a general sample injector.

SUMMARY

To solve the problems in the prior art, an objective of the present invention is to provide a general sample injector having simple structure, fast continuous sample injection and good detection effect on samples with a wide boiling range. The inventor recognized that the uniform temperature of a vaporizing chamber, the preheating of carrier gas and the full mixture of samples may eliminate split discrimination.

To achieve the above objective, according to one aspect of the present invention, a sample injector is provided. The sample injector includes a sample injector shell and a vaporizing chamber located in the sample injector shell;

a sample injector shell opening and a detachable end cover are arranged at the top of the sample injector shell, and the end cover seals the sample injector shell opening;

a vaporizing chamber opening is arranged at the top of the vaporizing chamber, and a channel for enabling a gas to pass is reserved between the vaporizing chamber opening and the end cover;

a carrier gas channel, a septum purge channel and a coolant channel are further arranged in the sample injector shell along the outer circumference of the vaporizing chamber, a carrier gas channel opening portion and a septum purge channel opening portion are respectively arranged at the tops of the carrier gas channel, the coolant channel and the septum purge channel, and both of the carrier gas channel opening portion and the septum purge channel opening portion are communicated with the opening at the top of the vaporizing chamber; the carrier gas channel is provided with a carrier gas inlet, the septum purge channel is provided with a septum purge channel outlet, and the coolant channel is provided with a coolant inlet and a coolant outlet;

a capillary column is arranged at the bottom of the vaporizing chamber, one end of the capillary column projects into the vaporizing chamber, and the other end of the capillary column projects out of the sample injector;

a heater is further arranged in the sample injector shell.

Preferably, a inlet liner is fixed in the vaporizing chamber, the two ends of the inlet liner are open, the opening at the top of the inlet liner is communicated with the opening at the top of the vaporizing chamber, and the opening at the bottom of the inlet liner is not in contact with the bottom of the vaporizing chamber;

a gap for enabling the gap to pass is reserved between the outer surface of the inlet liner and the inner surface of the vaporizing chamber;

a ring-shaped sealing and fixing device is arranged at the outer edge of the opening at the top of the inlet liner and at the inner edge of the opening of the vaporizing chamber; the inlet liner penetrates through the ring-shaped sealing device to fix the outer edge of the opening at the top of the inlet liner in the vaporizing chamber.

Preferably, the sealing ring is made from a high temperature resistant rubber material or a graphite material.

Preferably, the sample injector further includes a flow splitting channel, the flow splitting channel is provided with a flow splitting channel opening and a flow splitting channel outlet, and the flow splitting channel opening is arranged on the side wall of the vaporizing chamber and is communicated with the vaporizing chamber.

Preferably, the coolant channel is further communicated with the vaporizing chamber.

Preferably, a sealing septum is further arranged between the sample injector shell opening and the detachable end cover, and a channel for enabling the gas to pass is reserved between the sealing septum and the vaporizing chamber opening.

Preferably, the carrier gas inlet, the septum purge channel outlet, the coolant inlet and the coolant outlet are all arranged at the bottom of the sample injector shell.

Preferably, the inlet of the carrier gas channel, the outlet of the septum purge channel and the inlet and the outlet of the coolant channel are all connected with a gas flow control valve.

Preferably, the heaters are uniformly distributed on the outer wall of the sample injector shell, a temperature control unit is further included, and the heaters are controlled by the temperature control unit to achieve single-point heating or programmed temperature heating.

Preferably, the inlet of the carrier gas channel, the outlet of the septum purge channel and the inlet and the outlet of the coolant channel are all connected with the gas flow control valve, and the temperature control unit is further connected with the gas flow control valve; the temperature control unit and the gas flow control valve cooperate to cool the sample injector.

Preferably, the sample injector shell is made from a metallic material, and the center of the end cover and the center of the vaporizing chamber are coaxial.

Preferably, the capillary column is arranged just at the central position of the bottom of the vaporizing chamber.

The coolant channel functions as refrigerating and cooling the vaporizing chamber. During cooling, the coolant having large thermal capacity, including liquid nitrogen, liquid $CO_2$ or water, may be employed, or heat dissipation may be realized directly by nitrogen in atmosphere or air. When the liquid nitrogen or nitrogen is used for cooling, the coolant channel is communicated with the vaporizing chamber, and the coolant enters the vaporizing chamber from the coolant channel and flows along the flow splitting channel, the septum purge channel and a coolant outlet channel, so that the coolant plays a role of cooling and also purging the vaporizing chamber. When the non-inert coolant is used for cooling, the coolant channel undergoes reflux on the sample injector shell and is not communicated with the vaporizing chamber. The heater is uniformly distributed on the outer wall of the sample injector shell, so that the uniform heating of the upper and lower portions of the sample injector is ensured.

The sample injector, equivalent to a programmed temperature injector combining splitting/no splitting with cold column head sample injection, gives full play to the advantages of various sample injection modes, overcomes a plurality of disadvantages, and has higher practicability and better flexibility.

According to another aspect of the present invention, a gas chromatograph is further disclosed. The gas chromatograph includes the sample injector according to any one of the above embodiments According to still another aspect of the present invention, a gas chromatography-ion mobility spectrometer is further disclosed. The gas chromatography-ion mobility spectrometer includes the sample injector according to any one of the above embodiments.

According to a further aspect of the present invention, a gas chromatography-mass spectrum combined spectrometer is further disclosed. The combined spectrometer includes the sample injector according to any one of the above embodiments.

The sample injector, the gas chromatography and the combined spectrometer provided by the present invention have the following significant technical effects:

1. A plurality of channels are provided in the length direction of the vaporizing chamber, and one of the channels is used as a carrier gas channel, so the carrier gas may be preheated to have enough thermal capacity before entering the vaporizing chamber, so that it is ensured that the sample is quickly and uniformly vaporized after entering the vaporizing chamber and then enters a capillary column, thereby reducing split discrimination and obtaining better results of detection.

2. Other channels used as a coolant channel, a septum purge channel and a flow splitting channel respectively are also disposed on the sample injector shell. The advantage of this design is that the thermal capacity of the metal shell is reduced by the plurality of channels, and the coolant and flowing on the sample injector shell carrier gas may take away the heat of the vaporizing chamber and thus cool the vaporizing chamber. By this design, both quick heating and quick cooling may be realized, and it is advantageous for quick continuous sample injection during processing a large number of detection tasks.

3. The heater of the sample injector provided by the present invention is uniformly distributed on the sample injector shell. The advantage of such a design is that the sample injector shell may be uniformly heated, quick heating may be realized, the uniform vaporizing of the sample may be ensured, and the split discrimination is reduced.

4. The coordinative control of the coolant channel, the multichannel airflow control valve and the temperature controller allows the sample injector to have a programmed temperature function. As different samples are different in volatility, a low temperature needs to be set to first volatilize some volatile substances or substances easy to crack at a high temperature, while non-volatile samples are heated to a high temperature for volatilization, so as to make each sample component reach the optimal volatilization. The detection of a sample having a wide boiling range may employ programmed temperature vaporizer injection, so the substances easy to thermally crack or coke may be effectively protected. The advantage of this design is that the sample injection, as a general sample injector for use, may effectively realize the analysis of a sample having a wide boiling range and eliminates split discrimination.

BRIEF DESCRIPTION OF THE DRAWINGS

FIG. 1 is a structure diagram of a sample injector according to an embodiment of the present invention.

Reference numerals in FIG. 1: 1—End cover; 2—sealing septum; 3—Sample injector shell; 4—Seal ring; 5—Vaporizing chamber; 6—Inlet liner; 7—Carrier gas channel; 8—Septum purge channel; 9—Flow splitting channel; 10—Coolant channel; 11—Coolant inlet; 12—Gas source inlet; 13—Mutichannel flow control valve; 14—Carrier gas inlet; 15—Split flow outlet; 16—Septum purge gas outlet; 17—Coolant outlet; 18—Main gas outlet; 19—Capillary column; 20—Heater; 21—Temperature controller; 22—Cross section of sample injector shell.

DETAILED DESCRIPTION OF THE PREFERRED EMBODIMENTS

The specific embodiments of the present invention are further described below in detail in conjunction with the accompanying drawings and the embodiments. The embodiments below are only used for illustrating the present invention, rather than limiting the scope of the present invention.

As shown in FIG. 1, the present invention provides a sample injector, including: a sample injector shell and a vaporizing chamber located in the sample injector shell; a sample injector shell opening and a detachable end cover are arranged at the top of the sample injector shell, and the end cover seals the sample injector shell opening; a vaporizing chamber opening is arranged at the top of the vaporizing chamber, and a channel for enabling a gas to pass is reserved between the vaporizing chamber opening and the end cover; a carrier gas channel, a septum purge channel and a coolant channel are further arranged in the sample injector shell along the outer circumference of the vaporizing chamber, a carrier gas channel opening portion and a septum purge channel opening portion are respectively arranged at the tops of the carrier gas channel, the coolant channel and the septum purge channel, and both of the carrier gas channel opening portion and the septum purge channel opening portion are communicated with the opening at the top of the vaporizing chamber; the carrier gas channel is provided with a carrier gas inlet, the septum purge channel is provided with a septum purge channel outlet, and the coolant channel is provided with a coolant inlet and a coolant outlet; a capillary column is arranged at the bottom of the vaporizing chamber, one end of the capillary column projects into the vaporizing chamber, and the other end of the capillary column projects out of the sample injector; a heater is further arranged in the sample injector shell. A detailed description of the sample injector provided by the present invention will be given below.

Referring to FIG. 1, according to an embodiment of the present invention, a sample injection port mechanism of a sample injector is located on the top of the sample injector and consists of an end cover 1 and a sealing septum 2. The end cover 1 is sheathed on a sample injector shell 3 through threads, so it is convenient for disassembling and convenient to place a disposable sample tube during sample injection of solid. A channel for enabling the gas to pass is reserved between the sealing septum and the vaporizing chamber opening.

The vaporizing chamber 5 is located inside the sample injector shell, a sealing septum 2 for sealing the vaporizing chamber and the sample injection port is provided between the vaporizing chamber 5 and the end cover 1, and the center of the end cover is coaxial with the center of the vaporizing chamber. When a gas or liquid sample is injected, a quartz or glass inlet liner may be placed inside the vaporizing chamber. When a solid sample is injected, a disposable sample tube with solid component absorbed thereon may be placed inside the vaporizing chamber. The two ends of the inlet liner are open, the opening at the top of the inlet liner is communicated with the opening at the top of the vaporizing chamber, and the opening at the bottom of the inlet liner is not in contact with the bottom of the vaporizing chamber; a gap for enabling the gap to pass is reserved between the outer surface of the inlet liner and the inner surface of the vaporizing chamber; a ring-shaped sealing and fixing device is arranged at the outer edge of the opening at the top of the inlet liner and at the inner edge of the opening of the vaporizing chamber; the inlet liner penetrates through the ring-shaped sealing device to fix the outer edge of the opening at the top of the inlet liner in the vaporizing chamber. Specifically:

The inlet liner or disposable sample tube 6 is tightly sealed and supported by an O-shaped seal ring 4 and placed at the middle of the vaporizing chamber 5.

A capillary column 19 is provided at the right center of the bottom of the vaporizing chamber 5. The capillary column 19 is fixed on the bottom of the vaporizing chamber via a seal gasket and a nut convenient to be disassembled.

A plurality of channels is uniformly provided inside the sample injector shell 3 along the outer circumference of the vaporizing chamber. The positions of the channels may be observed with reference to the cross section 22 of the sample injector shell. The outlets and inlets of all the channels are formed on the bottom of the sample injector shell and extend to the upper end of the sample injector along the length direction of the vaporizing chamber. The plurality of channels may be functionally divided into a carrier gas channel 7, a septum purge channel 8, a flow splitting channel 9 and a coolant channel 10, wherein a carrier gas inlet 14 is connected to a gas source inlet 12 via a valve, the carrier gas flows upward from the carrier gas inlet 14 on the bottom of the sample injector shell along the carrier gas channel, and then enters the vaporizing chamber from the inlet of the vaporizing chamber 5 after preheated; the septum purge channel 8 is communicated with the opening at the top of the vaporizing chamber and leads out from a septum purge outlet 16 on the bottom of the sample injector shell in the length direction of the sample injector shell; the flow splitting channel 9 enters the top of the vaporizing chamber through a clearance between the vaporizing chamber 5 and the inlet liner 6 from the bottom of the inlet liner, extends out from the vaporizing chamber 5 from the underneath of the seal ring 4 and leads out from the bottom split flow outlet 15 along the flow splitting channel on the sample injector shell. The coolant channel 10 is uniformly distributed around the vaporizing chamber 5. To achieve the purpose of quick cooling, the coolant channel is communicated with the vaporizing chamber. The coolant may enter the coolant channel 10 from a coolant inlet 11. When liquid nitrogen, nitrogen or other inert substances are used for cooling, the coolant channel 10 may be communicated with the vaporizing chamber, the coolant and the carrier gas simultaneously enter the vaporizing chamber for cooling the vaporizing chamber, and the coolant may flow out from a coolant outlet 17 along the septum purge channel 8, the flow splitting channel 9 and the coolant channel 10, so that the coolant plays roles of cooling the vaporizing chamber and also purging the vaporizing chamber. When other non-inert cooling substances are employed, the coolant channel 10 is an independent reflux channel, is not communicated with the vaporizing chamber 5, and plays a role of cooling only. The working states and working time sequences of the channels are realized by a multichannel airflow control valve 13. A main gas outlet 18 used for discharging gas is connected to the outlets of the plurality channels via the multichannel airflow control valve 13.

The heater 20 is uniformly distributed on the outer wall of the sample injector shell, so that uniform heating of the upper and lower portions of the sample injector is ensured. The heater 20 is controlled by the temperature control unit 21 to realize single-point heating or programmed temperature heating. The coordinative effect of the temperature control unit 21 and the multichannel airflow control valve 13 realizes the cooling of the sample injector. During detection of a sample having a wide boiling range, the programmed temperature function may be activated for sample injection, so that the cracking or coking of low boiling point positions may be effectively avoided, split discrimination may also be overcome, and the accuracy of the results of detection is ensured.

Preferably, the seal ring is made from high temperature resistant rubber material or graphite material, and the heater is a resistance wire or a mica sheet.

According to another aspect of the present invention, a gas chromatograph is further disclosed. The gas chromatograph includes the sample injector according to any one of the above embodiments According to another aspect of the present invention, a gas chromatography-ion mobility spectrometer is further disclosed, which includes the sample injector according to any one of the above embodiments.

According to another aspect of the present invention, a gas chromatography-mass spectrum combined spectrometer is further disclosed. The gas chromatography-mass spectrum combined spectrometer includes the sample injector according to any one of the above embodiments.

The foregoing specific embodiments are merely used for explaining the technical solutions of the present invention, but the present invention is not limited thereto. All improvements and substitutions of the above principle and based on the present invention shall fall into the protection scope of the present invention.

To sum up, the sample injector, the gas chromatography and the combined spectrometer provided by the present invention have the following significant technical effects: 1. A plurality of channels are provided in the length direction of the vaporizing chamber, and one of the channels is used as a carrier gas channel, so the carrier gas may be preheated to have enough thermal capacity before entering the vaporizing chamber, to ensure that the sample is quickly and uniformly vaporized after entering the vaporizing chamber and then enters a capillary column, thereby reducing split discrimination and obtaining better results of detection. 2. Other plurality of channels used as a coolant channel, a septum purge channel and a flow splitting channel respectively are also disposed on the sample injector shell. The advantage of this design lies in that on the one hand, the thermal capacity of the metal shell is reduced by the plurality of channels, and on the other hand, the coolant and flowing on the sample injector shell and the carrier gas can take away the heat of the vaporizing chamber and thus cool the vaporizing chamber. By this design, both quick heating and quick cooling can be achieved, and it is advantageous for quick continuous sample injection during processing a large number of detection tasks. 3. The heater of the sample injector provided by the present invention is uniformly distributed on the sample injector shell. The advantage of such a design is that the sample injector shell may be uniformly heated, quick heating may be realized, the uniform vaporizing of the sample may be ensured, and the split discrimination is reduced. 4. The coordinative control of the coolant channel, the multichannel airflow control valve and the temperature controller allows the sample injector to have a programmed temperature function. As different samples are different in volatility, a low temperature needs to be set to first volatilize some volatile substances or substances easy to crack at a high temperature, while non-volatile samples are heated to a high temperature for volatilization, so as to make each sample component reach the optimal volatilization. The detection of a sample having a wide boiling range may employ programmed temperature vaporizer injection, such that the substances easy to thermally crack or coke may be effectively protected. The advantage of this design is that the sample injection, as a sample injector for use, may effectively realize the analysis of a sample having a wide boiling range and eliminates split discrimination.

INDUSTRIAL APPLICABILITY

To sum up, the sample injector, the gas chromatography and the combined spectrometer provided by the present invention have the following willful technical effects: 1. A plurality of channels are provided in the length direction of the vaporizing chamber, and one of the channels is used as a carrier gas channel, so the carrier gas may be preheated to have enough thermal capacity before entering the vaporizing chamber, so as to ensure that the sample is quickly and uniformly vaporized after entering the vaporizing chamber and then enters a capillary column, thereby reducing split discrimination and obtaining better results of detection. 2. Other plurality of channels used as a coolant channel, a septum purge channel and a flow splitting channel respectively are also disposed on the sample injector shell. The advantage of this design lies in that one the one hand, the thermal capacity of the metal shell is reduced by the plurality of channels, and on the other hand, the coolant and flowing on the sample injector shell and the carrier gas can take away the heat of the vaporizing chamber and thus cool the vaporizing chamber. By this design, both quick heating and quick cooling can be achieved, and it is advantageous for quick continuous sample injection during processing a large number of detection tasks. 3. The heater of the sample injector provided by the present invention is uniformly distributed on the sample injector shell. The advantage of such a design is that the sample injector shell may be uniformly heated, quick heating may be realized, the uniform vaporizing of the sample may be ensured, and the split discrimination is reduced. 4. The coordinative control of the coolant channel, the multichannel airflow control valve and the temperature controller allows the sample injector to have a programmed temperature function. As different samples are different in volatility, a low temperature needs to be set to first volatilize some volatile substances or substances easy to crack at a high temperature, while non-volatile samples are heated to a high temperature for volatilization, so as to make each sample component reach the optimal volatilization. The detection of a sample having a wide boiling range may employ programmed temperature vaporizer injection, so the substances easy to thermally crack or coke may be effectively protected. The advantage of this design is that the sample injection, as a general sample injector for use, may effectively realize the analysis of a sample having a wide boiling range and eliminates split discrimination.

The invention claimed is:

1. A sample injector, comprising:
   a sample injector shell;
   a vaporizing chamber located in the sample injector shell;
   a sample injector shell opening and a detachable end cover arranged at the top of the sample injector shell, the detachable end cover sealing the sample injector shell opening;
   a vaporizing chamber opening arranged at the top of the vaporizing chamber, wherein a channel for enabling a gas to pass is reserved between the vaporizing chamber opening and the end cover;
   a carrier gas channel, a septum purge channel and a coolant channel further arranged in the sample injector shell around an outer circumference of the vaporizing chamber, a carrier gas channel opening portion and a septum purge channel opening portion being respectively arranged at the tops of the carrier gas channel and the septum purge channel, and both the carrier gas channel opening portion and the septum purge channel opening portion being in communication with the vaporizing chamber opening;
   wherein the carrier gas channel is provided with a carrier gas inlet, the septum purge channel is provided with a septum purge channel outlet, and the coolant channel is provided with a coolant inlet and a coolant outlet;
   wherein the septum purge channel and the carrier gas channel are configured to flow the gas in opposite directions within the sample injector shell;
   a capillary column arranged at the bottom of the vaporizing chamber, one end of the capillary column projecting into the vaporizing chamber, and the other end of the capillary column projecting out of the sample injector; and
   one or more heaters further arranged in or on the sample injector shell.

2. The sample injector according to claim 1, further comprising:
   an inlet liner fixed in the vaporizing chamber, the two ends of the inlet liner being open, an opening at the top of the inlet liner being in communication with the vaporizing chamber opening, and an opening at the bottom of the inlet liner not being in contact with the bottom of the vaporizing chamber;
   a gap for enabling the gas to pass reserved between an outer surface of the inlet liner and an inner surface of the vaporizing chamber; and
   a ring-shaped sealing and fixing device arranged at an outer edge of the opening at the top of the inlet liner and at an inner edge of the vaporizing chamber opening;
   wherein the inlet liner penetrates through the ring-shaped sealing and fixing device to fix the outer edge of the opening at the top of the inlet liner in the vaporizing chamber.

3. The sample injector according to claim 2, wherein the ring-shaped sealing and fixing device is made from a high temperature resistant rubber material or a graphite material.

4. The sample injector according to claim 3, further comprising: a flow splitting channel, the flow splitting channel comprising a flow splitting channel opening and a flow splitting channel outlet, and the flow splitting channel opening being arranged on the side wall of the vaporizing chamber and being in communication with the vaporizing chamber.

5. The sample injector according to claim 2, further comprising: a flow splitting channel, the flow splitting channel comprising a flow splitting channel opening and a flow splitting channel outlet, and the flow splitting channel opening being arranged on the side wall of the vaporizing chamber and being in communication with the vaporizing chamber.

6. The sample injector according to claim 1, further comprising: a flow splitting channel, the flow splitting channel comprising a flow splitting channel opening and a flow splitting channel outlet, and the flow splitting channel opening being arranged on a side wall of the vaporizing chamber and being in communication with the vaporizing chamber.

7. The sample injector according to claim 1, wherein the coolant channel is in communication with the vaporizing chamber.

8. The sample injector according to claim 1, further comprising: a sealing septum arranged between the sample injector shell opening and the detachable end cover, wherein a channel for enabling the gas to pass is reserved between the sealing septum and the vaporizing chamber opening.

9. The sample injector according to claim 1, wherein the carrier gas inlet, the septum purge channel outlet, the coolant inlet and the coolant outlet are all arranged at the bottom of the sample injector shell.

10. The sample injector according to claim 9, wherein the carrier gas inlet, the septum purge channel outlet, the coolant inlet and the coolant outlet are all connected to a gas flow control valve.

11. The sample injector according to claim 1, wherein the carrier gas inlet, the septum purge channel outlet, the coolant inlet and the coolant outlet are all connected to a gas flow control valve.

12. The sample injector according to claim 1, wherein the one or more heaters are uniformly distributed on an outer wall of the sample injector shell, and the one or more heaters are controlled by a temperature control unit to achieve single-point temperature heating or programmed temperature heating.

13. The sample injector according to claim 12, wherein the carrier gas inlet, the septum purge channel outlet, the coolant inlet and the coolant outlet are all connected to a gas flow control valve, and the temperature control unit is further connected to the gas flow control valve;

wherein the temperature control unit and the gas flow control valve are configured to cooperate to cool the sample injector.

14. The sample injector according to claim 1, wherein the sample injector shell is made from a metallic material, and the center of the detachable end cover and the center of the vaporizing chamber are coaxial.

15. The sample injector according to claim 1, wherein the capillary column is arranged at a central position at the bottom of the vaporizing chamber.

16. A gas chromatograph, comprising the sample injector according to claim 1.

17. A combined spectrometer, which is a gas chromatography-ion mobility spectrometer and comprises the sample injector according to claim 1.

18. A combined spectrometer, which is a gas chromatography-mass spectrometer and comprises the sample injector according to claim 1.

* * * * *

UNITED STATES PATENT AND TRADEMARK OFFICE
CERTIFICATE OF CORRECTION

PATENT NO. : 9,618,484 B2
APPLICATION NO. : 14/577603
DATED : April 11, 2017
INVENTOR(S) : Qingjun Zhang et al.

Page 1 of 1

It is certified that error appears in the above-identified patent and that said Letters Patent is hereby corrected as shown below:

In the Claims

In Column 10, Line 51:
Replace "channel outlet, and the flow splitting channel" with --channel outlet, the flow splitting channel--.

Signed and Sealed this
Twenty-seventh Day of August, 2019

Andrei Iancu
*Director of the United States Patent and Trademark Office*